United States Patent

Miller et al.

[11] Patent Number: 5,515,718
[45] Date of Patent: May 14, 1996

[54] METHOD AND APPARATUS FOR DETERMINING TOUGHNESS OF BAKED PRODUCTS

[75] Inventors: Rebecca A. Miller; Russell C. Hoseney, both of Manhattan, Kans.

[73] Assignee: Kansas State University Research Foundation, Manhattan, Kans.

[21] Appl. No.: 327,855

[22] Filed: Oct. 24, 1994

[51] Int. Cl.[6] .............................. G01N 3/42; G01N 33/10
[52] U.S. Cl. .................................................. 73/81; 73/169
[58] Field of Search ................................. 73/81, 85, 169, 73/78

[56] References Cited

U.S. PATENT DOCUMENTS

| | | | |
|---|---|---|---|
| 2,481,467 | 9/1949 | Bloom et al. | 73/78 |
| 3,214,967 | 11/1965 | Bouschart et al. | 73/81 |
| 3,785,201 | 1/1974 | Rubio et al. | 73/81 X |
| 5,035,904 | 7/1991 | Huang et al. | 426/243 |
| 5,099,682 | 3/1992 | Denomme et al. | 73/81 |

OTHER PUBLICATIONS

Karlsson, Microwave Induced Changes During Reheating of Bread; Sep. 25, 1991, University of Lund abstract, pp. 1–32, Appendix 1, Apx 2, Apx–3, pp. 1–3, & Appendix 4.

Rogers, et al.; Texture Characteristics of Reheated Bread, Cereal Chem. 67(2):188–191 (1990).

*Primary Examiner*—Thomas P. Noland
*Attorney, Agent, or Firm*—Hovey, Williams, Timmons & Collins

[57] ABSTRACT

Apparatus (10) is provided for measurement of the toughness of edible products such as breads and cheeses. The apparatus (10) preferably includes a texture analyzer (12) equipped with a load cell crossarm (18); a special sample holding device (14) is mounted on the analyzer (12) and includes a base (30) adapted to hold a sample (88) and equipped with a flexible elongated pull wire (34). A cover assembly (32) is positioned atop the sample (88) and includes retention pins (64–70) to hold the sample in a substantially stationary condition. In use, the pull wire (34) is coupled to crossarm (18) and the analyzer (12) is actuated to elevate the arm (18), thus pulling the wire (34) at least partially through the sample (88). The force required to pull the wire (34) through the sample (88) is taken as a measure of sample toughness.

9 Claims, 3 Drawing Sheets

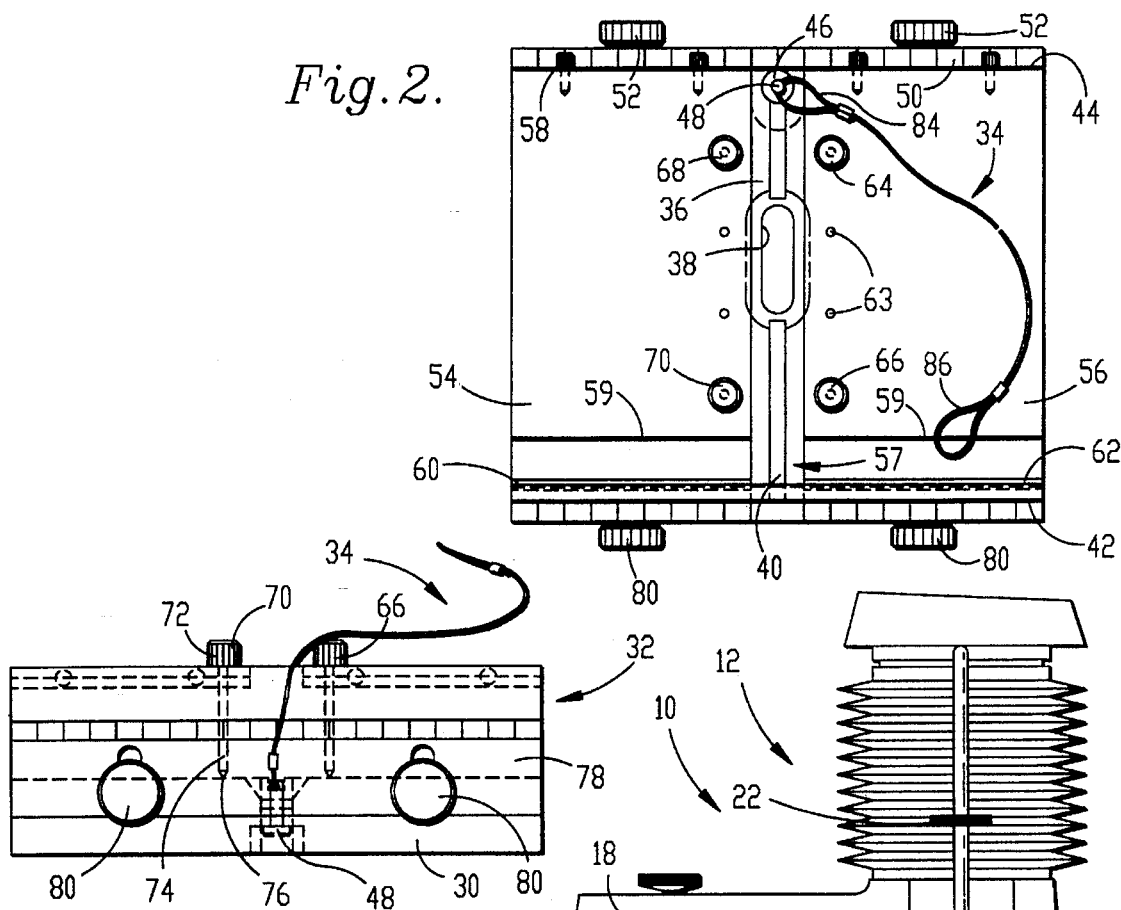
Fig.2.
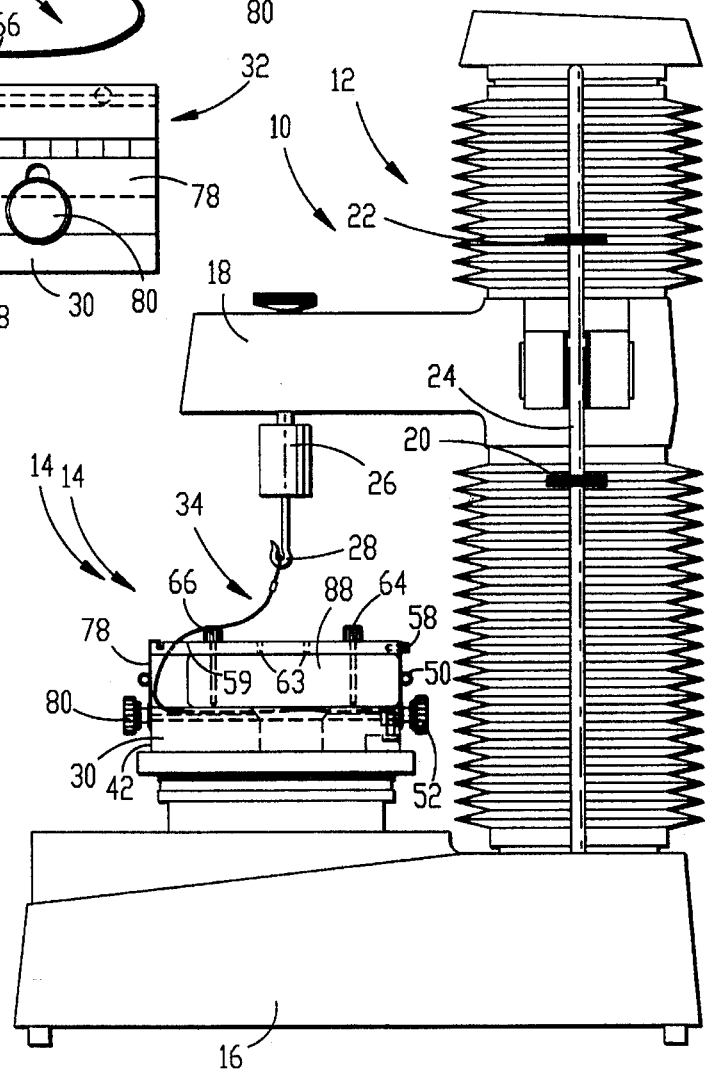
Fig.3.
Fig.1.

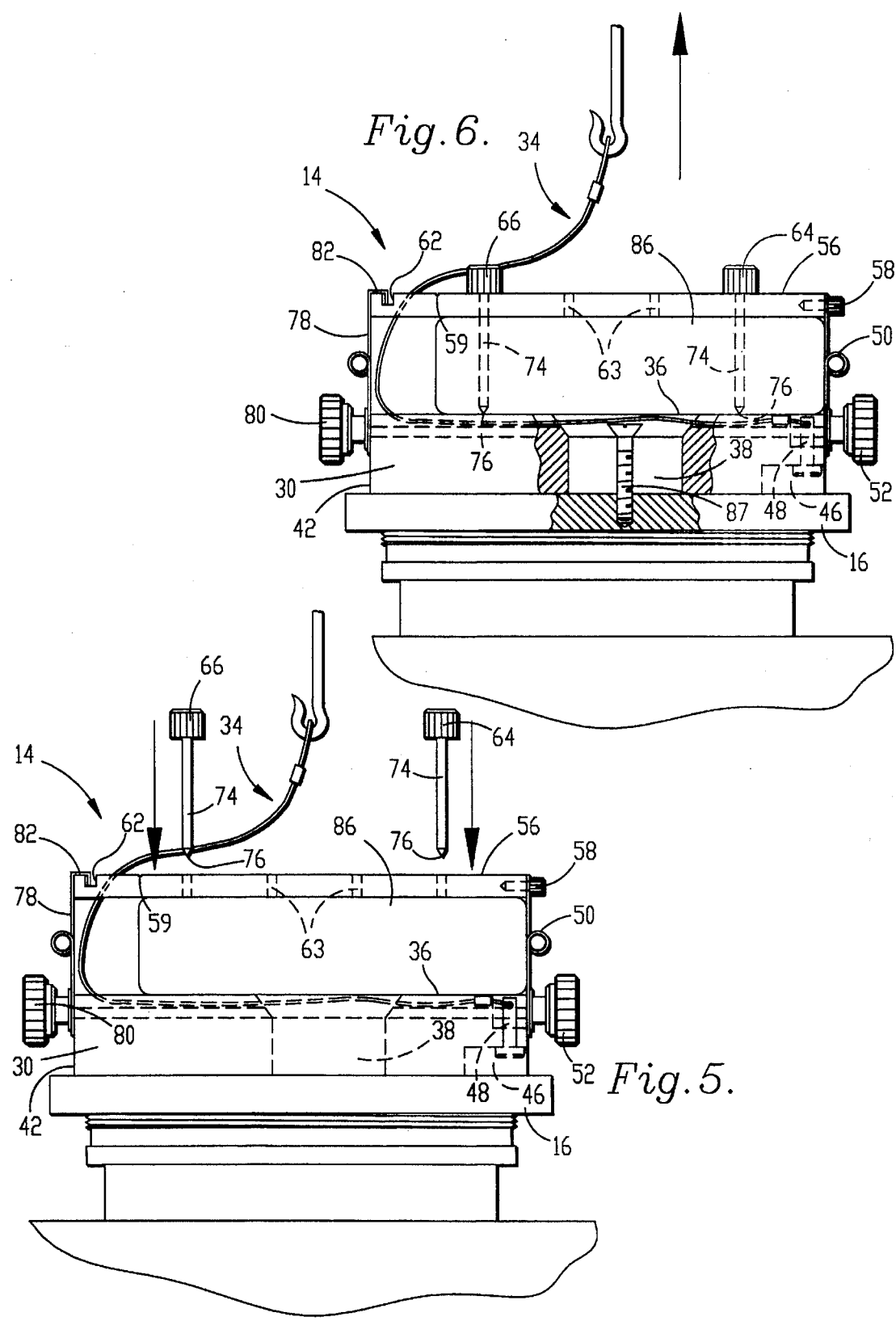

METHOD AND APPARATUS FOR DETERMINING TOUGHNESS OF BAKED PRODUCTS

BACKGROUND OF THE INVENTION

1. Field of the Invention

The present invention is broadly concerned with an improved method and apparatus for the testing of the toughness of products, particularly edible products such as bread, cheese and the like. More particularly, it is concerned with such a method and apparatus which gives accurate toughness measurements unaffected by factors such as staling, moisture content or outer crumb characteristics in the case of baked products.

2. Description of the Prior Art

It is well known that stale bread can be refreshened by heating. However, when the heating is done in a microwave oven the bread becomes tough (i.e. rubbery and hard to masticate). Several procedures to measure microwave-induced toughening of bread have been suggested. Rogers et al (1990) measured microwave-induced toughening of bread with the Instron Universal Testing Machine and the Kramer shear-compression cell attachment. They concluded that the peak force was related to organoleptic firmness and the shoulder force was related to organoleptic toughness. Marshall (1991) showed that the force deformation curves obtained from Kramer shear-compression cell analysis did not measure microwave-induced toughening of bread. The shoulder force was shown to be a combination of the force required to push the bread out of the bottom of the cell and the friction of the bread residue remaining in the cell and on the blades. The peak force was also shown to be indirectly correlated to the bread moisture content.

Dahle and Montgomery (1978) devised a method to measure bread staling which subjected a slice of bread to combined compression, shear, and tensile forces. In this method, a bread slice was centered on a platform over a cup. A disk of smaller diameter was attached to the crossarm of an Instron Universal Testing Machine. As the disk descended into the cup, the bread was deformed and ruptured. The point of bread rupture corresponded to the peak resistance and was termed "crumb strength". The distance from onset of deformation to point of peak resistance (displacement of the peak) was termed "crumb extensibility". Dahle and Sambucci (1987) applied the method to frozen bread which was thawed in a microwave oven. They noted an increase in crumb extensibility after microwave thawing. Karlsson (1991) used the method to analyze microwave reheated bread. The extensibility of the bread increased as microwave heating time increased and was selected as a measure of microwave-induced toughness.

However, it has been found that all of these prior techniques are deficient in that they fail to give a fully differentiated measure of microwave-induced toughness in bread products. These prior methods can be significantly influenced by staling, moisture content, outer crumb characteristics, or other factors not related to toughness of microwave reheated breads.

In addition, other types of products (e.g., cheese) exhibit toughness characteristics, and an accurate, differentiated method for measuring toughness in these contexts is also needed. There is accordingly a need in the art for an improved method and apparatus for the accurate determination of toughness of products, and particularly microwave reheated baked products.

SUMMARY OF THE INVENTION

The present invention overcomes the problems outlined above, and provides a greatly improved method and apparatus for the toughness testing of products particularly edible products such as breads and cheeses. Broadly speaking, the apparatus of the invention includes a product holding device having a surface for supporting a product sample thereon, and means for holding the product on the surface in a substantially stationary condition. An elongated wire is disposed proximal to the surface and beneath the product sample. The wire has a secured end and a free end, and is of a length sufficient to allow the free end of the wire to be pulled in order to cause the wire to pass at least partially through the product sample.

In preferred forms, the holding device includes a metallic base presenting the sample-supporting surface, wherein the base includes an elongated groove extending substantially between the opposed ends thereof. One end of the elongated wire is secured within the groove adjacent one end of the base and the wire extends along and within the groove substantially the full length of the base. The device further includes a cover assembly hingedly secured to the base. The cover assembly includes an elongated opening disposed above and in registry with the base groove, and moreover carries a plurality of product-piercing hold-down pins.

In use, a product sample is placed on the base surface, and the cover assembly is moved to a position atop the sample, so that the pins pierce and hold the sample in place. The free end of the wire is then attached to a load cell beam or other similar device, and is pulled upwardly through the stationary sample. The force required to pull the wire through the bread sample is a measure of product toughness.

BRIEF DESCRIPTION OF THE DRAWINGS

FIG. 1 is a side elevational view of toughness measuring apparatus in accordance with the invention, including a commercially available load cell-type analyzer and a specialized sample holding device for products;

FIG. 2 is a plan view of the preferred sample holding device of the invention;

FIG. 3 is an end view of the sample holding device of FIG. 2;

FIG. 5 is a side view illustrating the product holding device mounted on the analyzer base and with the free end of the pull wire of the device attached to the load cell arm of the analyzer;

FIG. 6 is a view similar to that of FIG. 5 with depicting the product-piercing pins in place and during the initial stages of a toughness measurement test wherein the wire is pulled upwardly to pass at least partially through the sample;

DETAILED DESCRIPTION OF THE PREFERRED EMBODIMENT

Figure 7:
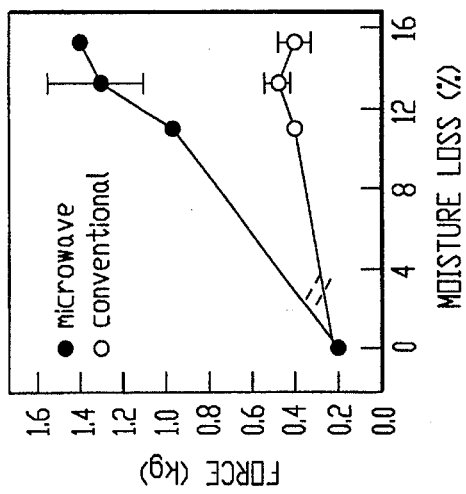
FIG. 7 is a graph of force versus percent moisture loss illustrating the force required to pull a wire through five-day old bread which was microwaved or conventionally reheated for heating times of 25, 30 and 35 seconds (microwave reheating) and 7, 9 and 11 minutes (conventional reheating) to produce moisture loss from the bread samples of 11%, 13% and 15%, respectively.

Turning now to the drawings, and particularly FIG. 1, preferred toughness testing apparatus 10 for products is illustrated. Broadly speaking, the apparatus 10 includes a commercially available TA.XT2 Texture Analyzer 12 and a specialized sample holding device 14.

In more detail, the analyzer 12 is comercialized by Stable Micro Systems, Haslemere, Surrey, UK. Analyzer 12 includes a base 16 supporting a vertically shiftable, horizontally extending load cell crossarm 18 in an elevated position above base 16. Movement of the crossarm is limited by stops 20, 22 located on upright guide spindle 24. Movement of the crossarm 18 is controlled through a separate console and stepper motor (not shown) and an appropriate recorder (also not shown) is coupled via the console in order to determine forces experienced by the load cell. A connector element 26 is secured to the outer end of arm 18 as shown, and terminates in a lowermost hook 28.

Figure 4:
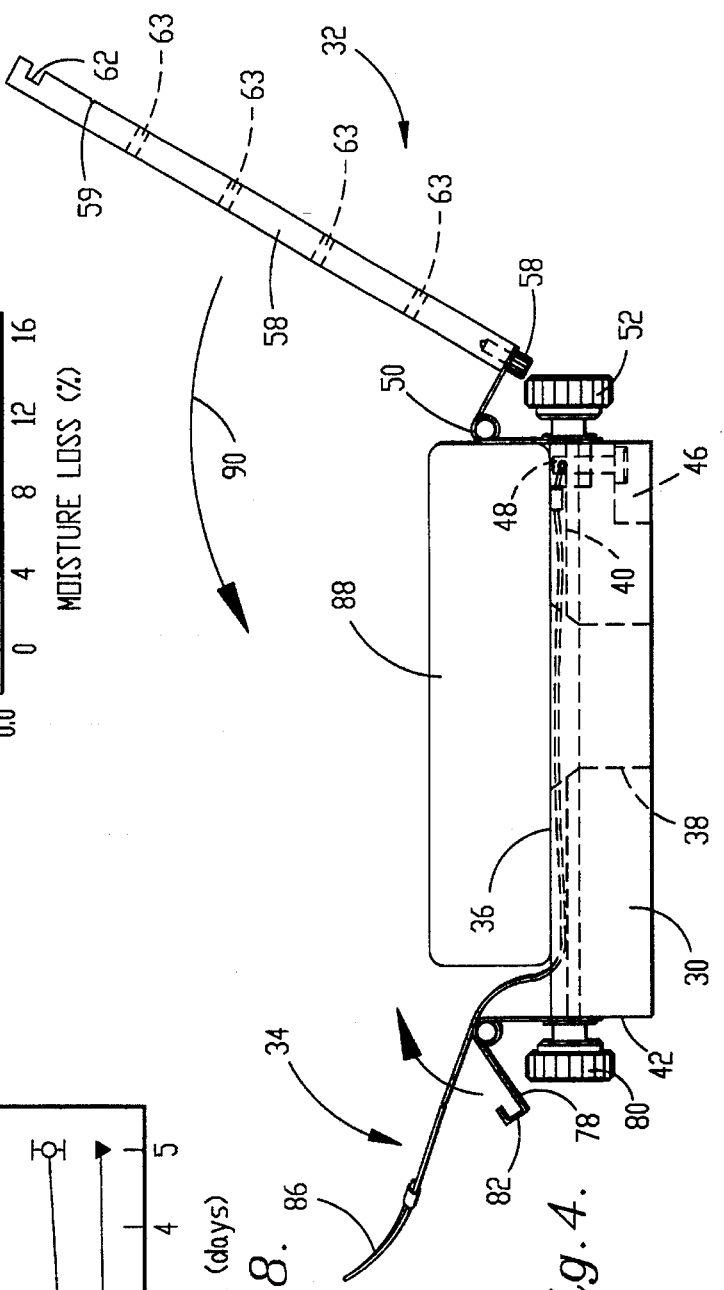
FIG. 4 is a side view illustrating the product holding device in an open condition with a bread sample placed on the device base.

The device 14 is best illustrated in FIGS. 2-4 and broadly includes a metallic aluminum base 30 as well as a cover assembly 32 and flexible pull wire 34. Referring particularly to FIGS. 2-3, it will be observed that the base 30 is in the form of a rectangular block member presenting an uppermost flat surface 36 adapted to support a product to be tested, such as a slice of bread or other baked product. Furthermore, the base 30 has an elongated connection opening 38 formed in the central region thereof as well as an elongated guide slot 40. The slot 40 extends essentially the full length of base 30 between the forward and rearward margins 42, 44 thereof. The end of slot 40 adjacent rearward margin 44 includes a generally circular depression 46 having the upper apertured end of connection screw 48 therein. As best illustrated in FIG. 3, the screw 48 extends upwardly from the recessed bottom of base 30 into the confines of depression 46.

The cover assembly 32 is hingedly secured to rear margin 40 of base 30 by means of an elongated, transverse, piano-type hinge 50. Threaded couplers 52 are employed for securing the lower end of hinge 50 to base 30. In addition, the overall assembly 32 includes a pair of transparent, laterally spaced, forwardly extending apertured cover members 54, 56 having a fore and aft extending opening 57 therebetween in substantial registry with underlying guide slot 40. The members 54, 56 are coupled to the upper margin of hinge 50 by means of short connection screws 58. The forward ends of the respective cover members 54, 56 are provided with transverse slots 60, 62 as shown; in addition, each member 54, 56 includes an etched product positioning line 59 proximal to and parallel with a corresponding slot 60 or 62. Each cover member 54, 56 also has a series of bores 63 therethrough, situated in spaced relationship along the inboard margin thereof. A pair of connector pins 64, 66 and 68, 70 are positioned within corresponding bores 63 and extend downwardly towards surface 36 of base 30. Referring to FIG. 3, it will be observed that each of the pins 64–70 includes an enlarged knurled head 72 as well as a depending shank 74 terminating in a pointed end 76.

A hingedly mounted keeper 78 is affixed to the forward margin 42 of base 30. The keeper 78 is likewise secured to the base 30 by means of couplers 80. The upper end of keeper 78 terminates in a somewhat U-shaped segment 82 (see FIG. 4), the end of which is configured to seat within the slots 60, 62 provided in the members 54, 56.

Pull wire 34 is formed of thin, flexible, metallic material and has a looped connection end 84. The end 84 is passed through the upper end of connection screw 48 as illustrated in FIG. 2, in order to secure the wire 34 adjacent rear margin 44. The wire 34 is of a length such that a portion thereof seats within guide slot 40, whereas the remainder passes upwardly through the opening 57 between cover members 54, 56. The outer or free end of wire 34 is also provided with a connection loop 86.

The use of apparatus 10 is best illustrated through a consideration of FIGS. 4-6, in the context of toughness testing of bread. In the first step, the device 14 is secured to base 16 of analyzer 12. This is accomplished by means of a conventional screw 87 (see FIG. 6) passing through opening 38 and into a tapped bore provided as a part of base 16. The cover assembly 32 is then moved to an open position exposing surface 36. At this point, the wire 34 is placed within slot 40 and thence extends upwardly as seen in FIG. 4. A prepared sample 88 of bread or other baked product is next placed on surface 36 over the portion of wire 34 located within guide slot 40. Next, the cover assembly 32 is closed by pivoting of the cover members 54, 56 in the direction of arrow 90 in FIG. 4 until the cover members are positioned closely atop sample 88. The bread sample may be accurately positioned by registration of an end margin thereof with the described etched lines 59 on cover members 54, 56. This condition is illustrated in FIG. 5, where it will be observed that the U-shaped segment 82 of keeper 78 is positioned within the slots 60, 62 of the cover members 54, 56. At this point, the pins 64–70 are inserted through the corresponding cover member opening 63 so that the pins pierce the sample 88 and contact surface 36. This condition is best illustrated in FIG. 6.

In the final step, the loop 86 at the free end of wire 34 is affixed to hook 28. The analyzer 12 is then operated to raise arm 18, thereby causing the wire 34 to be at least partially pulled through sample 88. The force required for passage of the wire through the sample is measured by the analyzer 12, and this is used to determine the toughness of the sample 88.

It will also be appreciated that the apparatus 10 could be used in a similar fashion with other types of product samples.

The following examples describe the use of the method and apparatus of the invention in the testing of toughness of reheated bread products. It is to be understood that the examples are provided by way of illustration only, and nothing therein should be taken as a limitation upon the overall scope of the invention.

EXAMPLES

In this study, bread loaves were reheated and tested for toughness using the preferred method and apparatus of the invention, versus a prior technique. The study confirmed that the method and apparatus of the invention could be used to measure microwave-induced toughness of bread and to differentiate between microwave reheated, conventionally reheated and unheated bread. Moreover, the technique of the invention was not affected by staling, bread moisture content, or outer crumb characteristics.

MATERIALS AND METHODS

Bread Preparation

The flour used was a commercially milled hard wheat flour containing 11.7% protein, 0.5% ash, and 13.7% moisture. Bread was baked as pup loaves using the AACC Method 10–10B straight-dough procedure. After the bread had cooled, it was placed in polyethylene bags and stored at room temperature until testing. Bread was tested 5 days after baking unless specified otherwise. The loaves were sliced into 25 mm thick slices weighing approximately 29 grams. The heels were discarded and the center three slices were used. Each slice was weighed before heating and after cooling to determine moisture loss during heating. Control bread was not heated. Crusts were removed from the bread slices after heating but before testing. Three loaves were used for each test.

Microwave Reheating

Bread slices were reheated in a Sharp Carousel II 750 watt microwave oven (Sharp Electronics Corp., Paramus, N.J.). An inverted 35 mm high styrofoam cup was placed on the center of the carousel. Slices of bread were heated on the cup to prevent moisture condensation under the bread during heating. The bread was microwave heated on high power for 25, 30, and 35 sec. The moisture loss from the bread slices was 11%, 13%, and 15%, respectively. After heating, the bread was cooled on a wire rack for 1 min. then placed in a polyethylene bag for 4 min. prior to testing.

Conventional Reheating

Slices of bread were placed directly on the rack in an air oven (model 28, Precision Scientific, Chicago, Ill.) set at 130° C. and heated for 7, 9, and 11 min. to obtain the same moisture loss produced by microwave heating for 25, 30, and 35 sec., respectively. After heating, the bread was placed on a wire rack in a polyethylene bag and allowed to cool for 5 min. prior to testing.

Bread Equilibration

Bread slices were reheated in the microwave or conventional oven for 35 sec. or 11 min., respectively. The bread was placed in polyethylene bags and held for 5 min., 30 min., 1 hr., and 8.5 hrs. to allow the moisture to equilibrate throughout the slice before testing.

Bread Aging

Bread was stored in polyethylene bags at room temperature for 1, 3, and 5 days after baking before testing. Bread slices were reheated in the microwave oven for 35 sec. or in the conventional oven for 11 min.

Toughness Testing—Prior Art Method

Bread toughness was measured using the TA.XT2 Texture Analyzer (Texture Technologies, Scarsdale, N.Y./Stable Micro Systems, Haslemere, Surrey, UK) with a slight modification of the method described by Dahle and Montgomery (1978). A slice of bread was centered on a cylinder having a 51 mm i.d. and 62 mm o.d. A 38 mm diameter aluminum disk probe was driven through the bread into the cylinder, thus deforming and rupturing the bread. The speed and distance traveled by the probe were 2.5 mm/sec. and 60 mm, respectively.

Toughness Testing—Preferred Wire-Cut Method

Bread toughness was taken as the amount of force required to pull a wire through a slice of bread. The bread was tested using the Texture Analyzer 12 and the device 14 shown in the drawings and described previously. Bread slices were placed on base 30 by unhooking keeper 78 and opening the cover members 54, 56. The bread was placed over the wire 34. The cover members 54, 56 were then moved down and the keeper 78 was snapped into place. The pointed pins 64–70 were inserted through the opening 63 into the bread to prevent sliding during testing.

As shown in the Figures, the Analyzer was fitted with a hook 28 on crossarm 18. The wire 34 was pulled through the bread perpendicular to the crossarm as the crossarm was raised. The Analyzer 12 was set to measure force in tension for a distance of 185 mm at a speed of 5 mm/sec. The trigger force was 5 grams. Peak force was recorded and taken as the measure of bread toughness.

Data Analysis

Data were evaluated by analysis of variance and least significant difference using the Statistical Analysis System (SAS Institute, Cary, N.C.).

RESULTS AND DISCUSSION

Prior Art Method

Karlsson (1991) reported that crumb extensibility, the distance from onset of deformation to point of peak resistance, was a measure of bread toughness. This measurement did not show a clear differentiation between microwave and conventionally reheated bread; therefore, crumb extensibility was not an appropriate measure of toughness. Several other parameters from the method developed by Dahle and Montgomery (1978) were analyzed to determine whether they correlated to microwave toughness. Peak force, area under the curve, and onset slope also failed to clearly differentiate between microwave and conventionally reheated bread. Therefore, the Dahle and Montgomery (1978) method was not an acceptable measure of microwave-induced toughness of bread.

Preferred Wire-Cut Method

In the new method, a wire was pulled through a slice of bread. The peak force required to cut the bread with the wire was taken as a measure of microwave-induced toughness. The force required to cut the microwave reheated bread was significantly higher than the conventionally reheated bread (FIG. 7). As the microwave heating time increased, the moisture content of the bread also decreased. To determine whether the toughness measurement was affected by moisture content, bread slices were reheated in the conventional oven to decrease the moisture content to the same level as the microwave reheated bread. Conventional heating time (moisture loss) did not affect peak force. This shows that the method hereof was not measuring bread moisture content. The amount of force increased as microwave heating time increased but the force did not change as the conventional reheating time increased. This confirms that microwave-induced toughening of bread is not caused by moisture loss.

Bread Equilibration

Microwaves penetrate bread, heating the center as well as the surface. Because microwaves do not heat air, the outer surface of the bread is cool. Water vapor migrates from the interior of the bread to the cooler surface and condenses, producing bread with a wet outer surface. The air in the oven is heated during conventional heating; therefore, the surface of the bread is hot. Water vapor from the surface migrates to the cooler interior of the bread, producing a dry outer surface. To determine whether the method and apparatus of the invention was sensitive to the outer surface characteristics of the bread, reheated bread slices were held for a period of time prior to testing to allow the moisture gradient within the slices to equilibrate. The force required to cut the microwave reheated bread was significantly higher than the conventionally reheated bread at all equilibration times (Table 1). The force increased significantly up to 30 minutes then held constant. Conventionally reheated bread tested immediately had a dry, brittle outer crust. With time this characteristic of the crust was lost. Although the outer crust characteristics changed, the force to cut the conventionally reheated bread remained significantly lower than the microwave reheated bread. This shows that the test was not measuring outer surface characteristics.

TABLE I

Effect of equilibration time on force required to pull a wire through bread slices which were reheated in the microwave or conventional oven for 35 sec. or 11 min., respectively.

| Heating method | Equilibration time (hours) | Peak force (g)[a] |
| --- | --- | --- |
| microwave | 0.08 | 527 b |
| microwave | 0.50 | 966 a |
| microwave | 1.00 | 842 a |
| microwave | 8.50 | 882 a |
| conventional | 0.08 | 278 c |
| conventional | 0.50 | 484 bc |
| conventional | 1.00 | 480 bc |
| conventional | 8.50 | 430 bc |

[a]different letters indicate significant differences (LSD = 244)

Bread Aging

Figure 8:
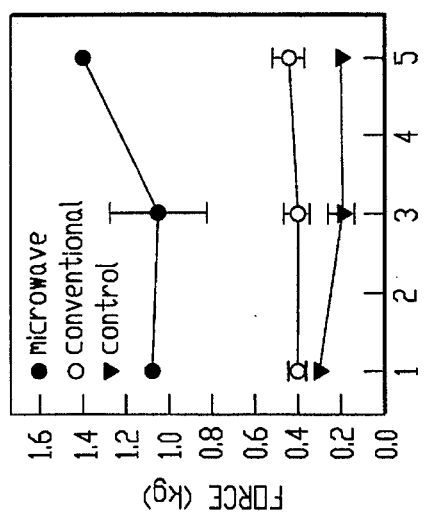
FIG. 8 is a graph of force versus bread age illustrating the effect of bread age on the force required to pull a wire through bread which was microwaved or conventionally reheated for 35 seconds or 11 minutes, respectively and as compared with unheated control bread.

The force required to cut the microwave reheated bread was significantly higher than the conventionally reheated and control (unheated) bread on all three days (FIG. 8). The force to cut the microwave reheated bread significantly increased on day 5. However, the force to cut the conventionally reheated and control bread did not change as the bread aged, showing that the test was not measuring bread firming.

Peak force measured by the preferred wire-cut method of the invention is a good measure of microwave-induced toughness in bread. The test clearly differentiated between microwave reheated, conventionally reheated, and unheated bread. The test was not affected by staling, moisture content, or outer crust characteristics.

REFERENCES

The following references are pertinent and/or mentioned herein. These references are incorporated by reference.

AMERICAN ASSOCIATION OF CEREAL CHEMISTS. 1983. Approved Methods of the AACC, 8th ed. Method 10–10B, approved January 1983, revised September 1985. The Association: St. Paul, Minn.

DAHLE, L. K. and MONTGOMERY, E. P. 1978. A method for measuring strength and extensibility of bread crumb. Cereal Chem. 55:197–203.

DAHLE, L. K. and SAMBUCCI, N. 1987. Application of devised universal testing machine procedures for measuring texture of bread and jam-filled cookies. Cereal Foods World 32:466–470.

KARLSSON, H. 1991. Microwave induced changes during reheating of bread. Diploma work. University of Lund, Sweden.

MARSHALL, E. S. 1991. Study of microwave induced toughening using the Kramer shear cell and differential scanning calorimeter. Masters thesis. Kansas State University, Manhattan.

ROGERS, D. E., DOESCHER, L. C., and HOSENEY, R. C. 1990. Texture characteristics of reheated bread. Cereal Chem. 67:188–191.

We claim:

1. Apparatus for determining the toughness of products, comprising:

a product holding device including a surface for supporting a product sample, and means for holding said product sample in a substantially stationary condition on said surface;

an elongated wire disposed proximal to said surface and beneath said product sample, said wire having a secured end and a free end, and being of a length sufficient to allow the free end of said wire to be pulled in order to cause the wire to pass at least partially through the product sample; and means operatively secured to the free end of said wire for pulling the wire at least partially through the product sample, and for measuring a physical parameter correlated with the toughness of said product sample.

2. Apparatus as set forth in claim 1, said holding device comprising:

a base presenting said sample-supporting surface and having a pair of opposed end margins, there being structure defining a groove in said base and in communication with said surface and extending substantially between said end margins;

a cover assembly operatively coupled with said base and movable between an open position permitting placement of said sample on said surface, and a sample holding position disposed atop said sample, said cover assembly including an elongated opening therein disposed above said groove when the cover assembly is in said sample-holding position thereof; and means securing one end of said wire within said groove and adjacent one of said end margins, said wire extending along the length of said groove and beneath said surface.

3. The apparatus of claim 2, including hinge means for coupling said cover assembly to said base.

4. The apparatus of claim 2, including a plurality of product sample piercing pin members carried by said cover assembly and adapted to pierce said product sample to hold the same in a substantially stationary condition on said surface.

5. The apparatus of claim 1, said wire pulling means including a vertically shiftable load cell arm, and means operatively coupling the free end of said wire with said arm.

6. A product sample holding device for facilitating measurement of the toughness of said sample, said device comprising:

structure defining a surface for supporting said sample thereon;

means for holding said sample in a substantially stationary condition on said surface; and an elongated wire disposed proximal to said surface and beneath said product sample, said wire having one end secured to said structure and a free end, and being of a length sufficient to allow the free end of said wire to be pulled in order to cause the wire to pass at least partially through the product sample.

7. The device of claim 6, said holding device comprising:

a base presenting said sample-supporting surface and having a pair of opposed end margins, there being structure defining a groove in said base and in communication with said surface and extending substantially between said end margins;

a cover assembly operatively coupled with said base and movable between an open position permitting placement of said sample on said surface, and a sample holding position disposed atop said sample, said cover assembly including an elongated opening therein disposed above said groove when the cover assembly is in said sample-holding position thereof; and means securing one end of said wire within said groove and adjacent one of said end margins, said wire extending along the length of said groove and beneath said surface.

8. The device of claim 7, including hinge means for coupling said cover assembly to said base.

9. The device of claim 7, including a plurality of product sample piercing pin members carried by said cover assembly and adapted to pierce said product sample to hold the same in a substantially stationary condition on said surface.

* * * * *